(12) United States Patent
Dekeyser et al.

(10) Patent No.: US 7,572,753 B2
(45) Date of Patent: Aug. 11, 2009

(54) TETRAZOLE FUNGICIDES

(75) Inventors: Mark A. Dekeyser, Waterloo (CA); Ahmad Ghavami, Guelph (CA); Robert G. Davis, Naugatuck, CT (US); Sheldon B. Park, Guelph (CA); Steven J. Hobbs, Wolcott, CT (US); Clifford Pratt, Bethel, CT (US); Gaik-Lean Chee, Guelph (CA); Daniel Walther, Cheshire, CT (US)

(73) Assignee: Chemtura Corporation, Middlebury, CT (US)

( * ) Notice: Subject to any disclaimer, the term of this patent is extended or adjusted under 35 U.S.C. 154(b) by 520 days.

(21) Appl. No.: 11/228,653

(22) Filed: Sep. 15, 2005

(65) Prior Publication Data

US 2007/0060631 A1    Mar. 15, 2007

(51) Int. Cl.
*A01N 43/713* (2006.01)
*C07D 257/04* (2006.01)
*C07D 409/04* (2006.01)

(52) U.S. Cl. .................. 504/261; 548/252; 548/254

(58) Field of Classification Search ............ 514/381, 514/382; 548/252, 253, 254, 250; 504/261
See application file for complete search history.

(56) References Cited

U.S. PATENT DOCUMENTS

| | | | | |
|---|---|---|---|---|
| 2,547,724 | A | 4/1951 | Sundholm | 167/33 |
| 3,865,570 | A | 2/1975 | George | 71/76 |
| 5,869,504 | A | 2/1999 | Dekeyser et al. | 514/340 |
| 6,020,355 | A | 2/2000 | Dekeyser et al. | 514/381 |
| 6,297,275 | B1 | 10/2001 | Dekeyser et al. | 514/486 |
| 6,451,835 | B1 | 9/2002 | Dekeyser et al. | 514/406 |
| 2004/0266738 | A1 | 12/2004 | Chee et al. | 514/150 |

FOREIGN PATENT DOCUMENTS

GB    1353699    5/1974
GB    1381840    1/1975

OTHER PUBLICATIONS

Buzilova et al., Journal of Organic Chemistry of USSR, pp. 1375-1379, (1989).
Janda et al., Chem. Papers, Synthesis of some substituted tetrazolylacetic acids, 43:63-71 (1989).
Brekhov et al., Journal of Organic Chemistry of USSR, pp. 1539-1542 (1993).
Verkhozina O.N. et al., Russian Journal of Organic Chemistry 39(12), pp. 1792-1796, 2003.

*Primary Examiner*—Kamal A Saeed
*Assistant Examiner*—Kristin Bianchi
(74) *Attorney, Agent, or Firm*—Jaimes Sher

(57) ABSTRACT

The use of certain tetrazole compounds as fungicides is disclosed wherein said compounds are of the structural formula:

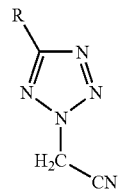

wherein:
R is selected from the group consisting of phenyl groups of the structural formula:

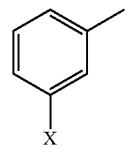

and thienyl groups of the structural formula:

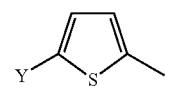

and
X and Y are each selected from the group consisting of hydrogen, haloalkyl, halogen, and nitro.

Novel compounds wherein X is selected from the group consisting of haloalkyl, halogen, and nitro and Y is selected from the group consisting of hydrogen, haloalkyl, halogen, and nitro are also disclosed.

11 Claims, No Drawings

TETRAZOLE FUNGICIDES

BACKGROUND OF THE INVENTION

1. Field of the Invention

The present invention relates to certain tetrazole derivatives that are useful as fungicides. More particularly, the present invention relates to a method for controlling fungi by contacting the fungi with a fungicidally effective amount of the tetrazole derivative compound, or by applying the tetrazole derivative compound to plant foliage or plant seed susceptible to attack by said fungi, or to a growth medium for the plant to be protected.

2. Description of Related Art

U.S. Pat. No. 3,865,570 discloses a method of regulating the growth of plants, which comprises applying to the plants a compound of the formula:

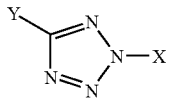

wherein Y is an aryl or heterocyclic group, optionally substituted, and X represents a hydrogen atom, a hydroxyalkyl group, a carboxylate ester group or a carboxyalkyl group, or a salt, ester, amide or nitrile thereof.

U.S. Pat. No. 5,869,504 discloses tetrazole derivatives of the formula

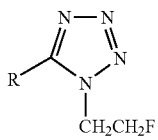

wherein R is a substituted or unsubstituted phenyl group, heterocyclic group, or benzo-fused heterocyclic group, which exhibit activity as insecticides and acaricides.

U.S. Pat. No. 6,020,355 discloses tetrazole derivatives of the formula

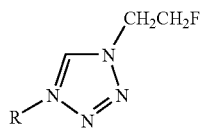

wherein R is a substituted or unsubstituted phenyl group, heterocyclic group, or benzo-fused heterocyclic group, which exhibit activity as insecticides and acaricides.

U.S. Pat. No. 6,297,275 discloses a method for controlling fungi using a phenylhydrazine derivative compound of the formula:

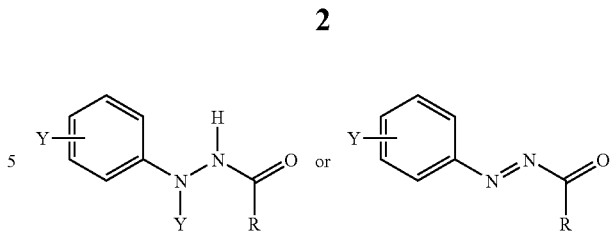

wherein: X is phenyl, phenylalkoxy, phenoxy, or benzyl, alone or in combination with one or more halogen, alkyl, or alkylthio; Y is hydrogen, alkanoyl, haloalkanoyl, or alkoxy carbonyl; and R is hydrogen, alkyl, haloalkyl, alkoxy, haloalkoxy, or phenylalkoxy.

U.S. Pat. No. 6,451,835 discloses fluoroethyl pyrazole compounds of the formula:

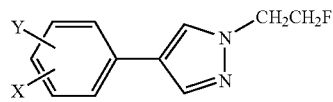

wherein X and Y are independently selected from the group consisting of hydrogen, halogen, alkyl, haloalkyl, nitro, alkylthio, alkylsulfinyl, alkylsulfonyl, and haloalkoxy. These compounds are useful as insecticides, nematicides, fungicides, and acaricides.

U.S. Patent Application Publication No. 2004/0266738 discloses certain phenoxyphenylhydrazine derivatives that are useful as fungicides.

U.K. Patent No. 1,353,699 discloses a method of regulating the growth of plants, which comprises applying for uptake by the plants a compound of the formula:

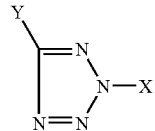

wherein Y is an aryl or heterocyclic group, optionally substituted, and X represents a hydrogen atom, a carboxylate ester group, a hydroxyalkyl group or a carboxyalkyl group, or a salt, ester amide or nitrile thereof.

U.K. Patent No. 1,381,840 is directed to tetrazole compounds useful in the method of U.K. Patent No. 1,353,699.

Buzilova, S. R. et al. (*Journal of Organic Chemistry of USSR*, pp. 1375-1379(1989)) disclose the synthesis of 1(2)-cyanoalkyltetrazoles by the alkylation of 5-substituted tetrazoles with chloroacetonitrile in dioxane in the presence of potassium hydroxide and triethylbenzylammonium chloride. 5-Cyanoalkyltetrazoles were synthesized as a result of the substitution of chlorine in 5-chloroalkyltetrazoles by a cyano group in the presence of dibenzo-18-crown-6 ether.

Janda, L. et al. (*Chem. Papers* 43:63-71 (1989)) disclose the preparation of a mixture of ethyl 5-(5-bromo-2-furyl)-1-tetrazolylacetate and ethyl 5-(5-bromo-2-furyl)-2-tetrazolylacetate by the alkylation of 5-(5-bromo-2-furyl)-1H-tetrazole with ethyl bromoacetate. The two products of the mixture were chromatographically separated and the ester substituted in position 1 was the substrate for the nucleophilic substitution with 4-substituted thiophenols. The resulting ethyl 5-[5-(4-R-phenylthio-2-furyl)-1-tetrazolylacetates were hydrolyzed to the corresponding acids.

Brekhov, Y. V. et al. (*Journal of Organic Chemistry of USSR*, pp 1539-1542 (1993)) disclose a series of derivatives of C- and N-substituted cyanomethyltetrazoles that were brought into alkylation, condensation, addition to multiple bonds, dimerization, and azo coupling reactions. The chemical reactivity of the methylene fragment is said to increase in the series of 5-, 1-, and 2-cyanomethyltetrazoles.

Verkhozina, O. N. et al. (*Russian Journal of Organic Chemistry* 39(12), pp 1792-1796 (2003)) disclose the synthesis of polynuclear blocks consisting of nonfused heterocycles of the azole series, connected through methylene bridges, by successive addition of azole units via cycloaddition of organic azides to the triple bond of N-(2-propynyl)azoles, as well as via reaction of azide ion at the cyano group of cyanomethylazoles. Initial N-(2-propynyl)azoles were prepared by reaction of 2-propynyl bromide with 1,2,3-triazoles, benzotriazole. and tetrazoles; cyanomethylazoles were obtained by alkylation of azoles with chloroacetonitrile. An analogous scheme was used to add heterocyclic units to 2-phenyl-1,2,3-triazole-4-carbonitrile. In this case, the first two heterocyclic units are linked through the ring carbon atom.

The disclosures of the foregoing are incorporated herein by reference in their entirety.

SUMMARY OF THE INVENTION

It is an object of this invention to provide novel tetrazole derivative compounds and compositions.

It is a further object of this invention to provide a method for controlling fungi using the tetrazole derivative compounds and compositions.

These and other objects are achieved by the present invention, which is directed to tetrazole compounds of the structural formula:

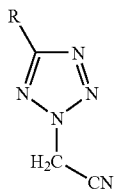

wherein:

R is selected from the group consisting of phenyl groups of the structural formula:

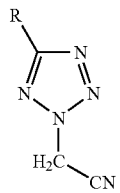

and thienyl groups of the structural formula:

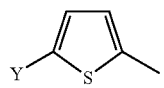

X is selected from the group consisting of haloalkyl, halogen, and nitro, and

Y is selected from the group consisting of hydrogen, haloalkyl, halogen, and nitro.

In another aspect, the present invention is directed to a method for controlling fungi comprising contacting the fungi with a fungicidally effective amount of at least one tetrazole compound of the structural formula:

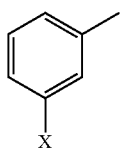

wherein:

R is selected from the group consisting of phenyl groups of the structural formula:

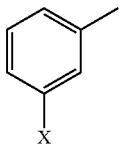

and thienyl groups of the structural formula:

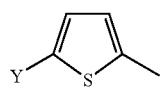

and

X and Y are each selected from the group consisting of hydrogen, haloalkyl, halogen, and nitro.

In still another aspect, the present invention is directed to a composition comprising (A) a fungicidally effective of a tetrazole compound of the structural formula:

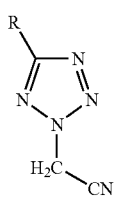

wherein:

R is selected from the group consisting of phenyl groups of the structural formula:

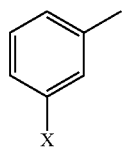

and thienyl groups of the structural formula:

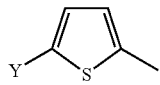

X and Y are each selected from the group consisting of hydrogen, haloalkyl, halogen, and nitro; and (B) a suitable carrier.

DESCRIPTION OF THE PREFERRED EMBODIMENT(S)

As stated above, the present invention is directed to the use of tetrazole compounds of the structural formula:

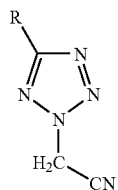

wherein:

R is selected from the group consisting of phenyl groups of the structural formula:

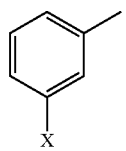

and thienyl groups of the structural formula:

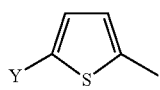

X and Y are each selected from the group consisting of hydrogen, haloalkyl, halogen, and nitro.

The compounds, per se, wherein X is selected from the group consisting of haloalkyl, halogen, and nitro and Y is selected from the group consisting of hydrogen, haloalkyl, halogen, and nitro are believed to be novel. The compound in which X is hydrogen is known in the art. See, Verkhozina, O. N. et al. (*Russian Journal of Organic Chemistry* 39(12), pp 1792-1796 (2003)).

Where X and/or Y is halogen, it may be either fluorine, chlorine, bromine, or iodine, preferably chlorine or bromine. Similarly, where X and/or Y is haloalkyl, the halo moiety may be either fluorine, chlorine, bromine, or iodine, preferably chlorine, bromine, of fluorine, more preferably fluorine, and the alkyl moiety is preferably lower alkyl of from one to four carbon atoms.

In a highly preferred embodiment, the compounds of the present invention are selected from the group consisting of those of the structure:

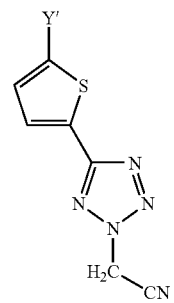

wherein Y' is chlorine or bromine.

The compounds of the present invention can be prepared by reacting a suitably substituted tetrazole of the formula:

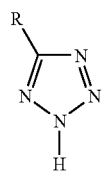

with a haloacetonitrile, e.g., bromoacetonitrile or chloroacetonitrile, in the presence of a base, such as triethylamine, potassium carbonate, or sodium hydride, in a solvent, such as acetonitrile or dimethylformamide, at temperatures in the range of from 0 to 100° C. The tetrazole can be prepared by methods known in the art, see, for example, *Chem. Papers* 43:63-71 (1989) and U.S. Pat. No. 3,865,570, the disclosures of which are incorporated herein by reference in their entirety.

This invention also relates to a method for controlling fungi comprising contacting the fungi with a fungicidally effective amount of at least one tetrazole compound of the structural formula:

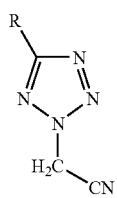

wherein:

R is selected from the group consisting of phenyl groups of the structural formula:

and thienyl groups of the structural formula:

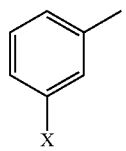

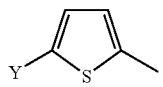

X and Y are each selected from the group consisting of hydrogen, haloalkyl, halogen, and nitro.

For the purposes of this invention, the term "controlling fungi" means inhibiting both future infestation and continued growth of existing infestations.

Compositions useful in the method of this invention comprise (a) a fungicidally effective of the tetrazole compound of the present having a structure described above, and (b) a suitable carrier. Such suitable carriers may be solid or liquid in nature. Suitable liquid carriers may be comprised of water, alcohols, ketones, phenols, toluene, and xylenes. In such formulations, additives conventionally employed in the art may be utilized, such as, for example, one or more surface active agents and/or inert diluents, to facilitate handling an application of the resulting pesticide composition.

The compositions useful in the method of this invention can alternatively comprise solid carriers taking the form of dusts, granules, wettable powders, pastes, aerosols, emulsions, emulsifiable concentrates, and water-soluble solids. For example, the compounds useful in the method of this invention can be applied as dusts when admixed with or adsorbed onto powdered solid carriers, such as mineral silicates, e.g., mica, talc, pyrophyllite, and clays, together with a surface-active dispersing agent so that a wettable powder is obtained which then is applicable directly to the loci to be treated. Alternatively, the powdered solid carrier containing the compound admixed therewith may be dispersed in water to form a suspension for application in such form.

Granular formulations of the compounds, suitable for application by broadcasting, side dressing, soil incorporation, or seed treatment, are suitably prepared using a granular or pellitized form of carrier, such as granular clays, vermiculite, charcoal, or corn cobs.

Alternatively, the compounds useful in the method of this invention can be applied in liquids or sprays when utilized in a liquid carrier, such as in a solution comprising a compatible solvent, such as acetone, benzene, toluene, or kerosene, or as dispersed in a suitable non-solvent medium, for example, water.

Another method of application to the loci to be treated is aerosol treatment, for which the compound may be dissolved in an aerosol carrier that is a liquid under pressure, but which is a gas at ordinary temperature (e.g., 20° C.) and atmospheric pressure. Aerosol formulations may also be prepared by first dissolving the compound in a less volatile solvent and then admixing the resulting solution with a highly volatile liquid aerosol carrier.

For treatment of plants (such term including plant parts), the compounds useful in the method of this invention preferably are applied in aqueous emulsions containing a surface-active dispersing agent which may be non-ionic, cationic, or anionic. Suitable surface-active agents include those known in the art, such as those disclosed in U.S. Pat. No. 2,547,724 (columns 3 and 4). The compounds of the invention may be mixed with such surface-active dispersing agents, with or without an organic solvent, as concentrates for the subsequent addition of water to yield aqueous suspensions of the compounds at desired concentration levels.

In addition, the compounds may be employed with carriers that are pesticidally active, such as insecticides, acaricides, fungicides, or bactericides.

It will be understood that the amount of the compound in a given formulation useful in the method of this invention will depend upon the specific fungus to be combatted, as well as upon the specific chemical composition and formulation of the compound being employed, the method of applying the compound/formulation, and the locus of treatment, so that the fungicidally effective amount of the compound may vary widely. Generally, however, concentrations of the compound as the active ingredient in fungicidally effective formulations in the method of this invention can range from about 0.1 to about 95 percent by weight. Spray dilutions may be as low as a few parts per million, while at the opposite extreme, full strength concentrates of the compound may be usefully applied by ultra low volume techniques. Concentration per unit area, where plants constitute the loci of treatment, may range between about 0.01 and about 50 pounds per acre, with concentrations of between about 0.1 and about 10 pounds per acre preferably being employed for crops such as corn, tobacco, rice, and the like.

To control fungi, sprays of the compounds can be applied to the fungi directly and/or to plants or plant seeds upon which they feed or nest. The fungicidally active formulations useful in the method of this invention can also be applied to the soil, water, or other growth medium in which the pests are present.

The specific methods of application, as well as the selection and concentration of the compounds useful in the method of this invention, will, of course, vary depending upon such circumstances as geographic area, climate, topography, plant tolerance, and the like. For specific circumstances, one skilled in the art may readily determine the proper compound, concentration, and method of application by routine experimentation.

Examples of phytopathogenic fungi that can be controlled by the method of this invention include, e.g., the following:

*Erysiphe graminis* f.sp. *hordei*
*Erysiphe cichoracearum*
*Erysiphe polygoni*
*Pyricularia grisea*
*Pyricularia oryzae*
*Helminthosporium sativum*
*Uromyces appendiculatus*
*Botrytis cinerea*
*Colletotrichum gossypii*
*Cercosporidium personatum*
*Fusarium nivale*
*Phytopthora infestans*
*Pythium ultimum*
*Rhizoctonia solani*
*Sclerotinia minor*
*Septoria nodorum*

Various features and aspects of the present invention are illustrated further in the examples that follow. While these examples are presented to show one skilled in the art how to operate within the scope of the invention, they are not intended in any way to serve as a limitation upon the scope of the invention.

EXAMPLES

Example 1 (Comparative)

Preparation of 5-phenyl-2H-tetrazole-2-acetonitrile (Compound 1)

To 146 mg (1 mmol) of 5-phenyltetrazole and 75 mg (1 mmol) of chloroacetonitrile was added three mL of dimethyl formamide. The resulting solution was stirred, then 158 mg (1 mmol) of potassium carbonate was added and the mixture was further stirred at room temperature for 18 hours. Twenty-five mL of water was then added and the mixture was extracted twice with 25 mL of ethyl acetate. Evaporation of the extracts left the crude product, which was purified by silica gel chromatography, leaving an oil that was pure by NMR.

Examples 2-8

The remaining compounds (Examples 2-8) listed in Table 1 were prepared according to the above procedure. The identity of each of the compounds was confirmed by NMR spectroscopy.

TABLE 1

Fungicidal Tetrazole Derivatives

| Example | R | $^1$NMR Data (CDCl$_3$) |
| --- | --- | --- |
| 1 | C$_6$H$_5$ | s (2) 5.6; m (5) 7.0-7.8 |
| 2 | 3-ClC$_6$H$_4$ | s (2) 5.6; m (4) 7.5-8.2 |
| 3 | 3-CF$_3$C$_6$H$_4$ | s (2) 5.6; m (4) 7.6-8.4 |
| 4 | 3-FC$_6$H$_4$ | s (2) 5.6; m (4) 7.2-8.0 |
| 5 | 3-BrC$_6$H$_4$ | s (2) 5.6; m (4) 7.3-8.3 |
| 6 | 5-Br-2-C$_4$H$_2$S | s (2) 5.6; d (1) 7.1 d (1) 7.1 |
| 7 | 5-Cl-2-C$_4$H$_2$S | s (2) 5.6; d (1) 6.9 d (1) 7.5 |
| 8 | 5-NO$_2$-2-C$_4$H$_2$S | s (2) 5.6; d (1) 7.8 d (1) 7.9 |

Biological Tests

Foliar Spray for the Control of Rice Blast Caused by *Pyricularia oryzae*

Technical grade material (active ingredient) is formulated in DMSO (1.5%), acetone (15%), Tween (0.1%), and water (83.4%) to provide a concentration of 300 ppm (w/v). The solutions are sprayed to near run-off onto 7-days-old greenhouse-grown rice (var. "Lemont") plants at the cotyledon stage (approx. 10 plants/pot in Fafard® horticultural mix). Treated plants are inoculated within 24 hours from spraying with an aqueous suspension of approximately 200,000 conidia/mL of the rice blast pathogen *Pyricularia oryzae* grown on a mycological agar. Inoculated plants are placed into a high humidity chamber for four days and then transferred to the greenhouse for two days prior to estimating the percent of diseased leaf area. Activity is calculated by dividing the difference between the percent disease on plants treated with inert formulation ingredients and the percent disease of plants treated with the active ingredient by the percent disease on plants treated with inert formulation ingredients.

Examples of activity against foliar rice blast after spray applications are shown below in Table 2.

TABLE 2

Percent (%) disease control by cyanomethyl tetrazoles at 300 ppm in greenhouse foliar application sprays

| Example | Rice Blast |
| --- | --- |
| 1 | 70 |
| 2 | 93 |
| 3 | 95 |
| 4 | 80 |
| 5 | 100 |
| 6 | 100 |
| 7 | 100 |
| 8 | 90 |

In view of the many changes and modifications that can be made without departing from principles underlying the invention, reference should be made to the appended claims for an understanding of the scope of the protection to be afforded the invention.

What is claimed is:

1. A tetrazole compound of the structural formula:

wherein:
R is selected from the group consisting of phenyl groups of the structural formula:

and thienyl groups of the structural formula:

X is selected from the group consisting of haloalkyl, halogen, and nitro, and
Y is selected from the group consisting of hydrogen, haloalkyl, halogen, and nitro.

2. The compound of claim 1 wherein Y is selected from the group consisting of haloalkyl, halogen, and nitro.

3. The compound of claim 1 wherein said compound is of the structure:

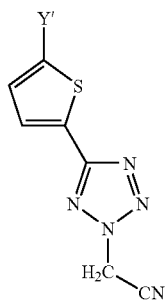

wherein Y' is chlorine or bromine.

4. A composition comprising
(A) a fungicidally effective amount of a tetrazole compound of the structural formula:

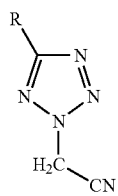

wherein:
R is selected from the group consisting of phenyl groups of the structural formula:

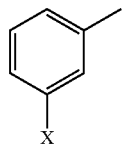

and thienyl groups of the structural formula:

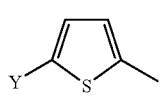

X is selected from the group consisting of haloalkyl, halogen, and nitro, and Y is selected from the group consisting of hydrogen, haloalkyl, halogen, and nitro; and
(B) a suitable carrier.

5. The composition of claim 4 wherein R is a substituted phenyl group and X is selected from the group consisting of haloalkyl, halogen, and nitro.

6. The composition of claim 4 wherein R is a substituted thienyl group and Y is selected from the group consisting of haloalkyl, halogen, and nitro.

7. The composition of claim 4 wherein the tetrazole compound is of the structure:

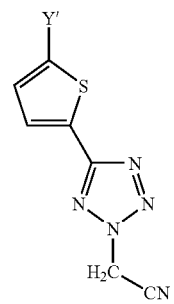

wherein Y' is chlorine or bromine.

8. A tetrazole of the structural formula:

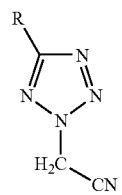

wherein:
R is selected from the group consisting of phenyl groups of the structural formula:

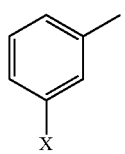

and thienyl groups of the structural formula:

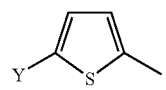

X is selected from the group consisting of haloalkyl, halogen, and nitro, and
Y is selected from the group consisting of haloalkyl, halogen, and nitro.

9. The compound of claim 8, wherein the tetrazole compound is of the structure:

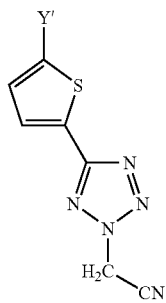

wherein Y' is chlorine or bromine.

10. A composition comprising
  (A) a fungicidally effective amount of a tetrazole compound of the structural formula:

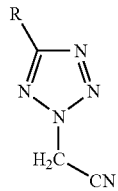

wherein:
  R is a thienyl group of the structural formula:

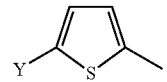

Y is selected from the group consisting of haloalkyl, halogen, and nitro; and
  (B) a suitable carrier.

11. The composition of claim 10, wherein the tetrazole compound is of the structure:

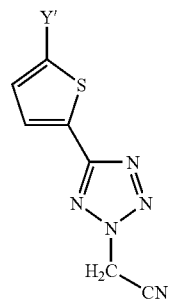

wherein Y' is chlorine or bromine.

* * * * *